United States Patent [19]

Matthews

[11] Patent Number: 4,867,442
[45] Date of Patent: Sep. 19, 1989

[54] PHYSICAL EXERCISE AID

[76] Inventor: H. Gerard Matthews, 19 Russell Rd., Haddam, Conn. 06438

[21] Appl. No.: 107,269

[22] Filed: Oct. 9, 1987

[51] Int. Cl.⁴ ............................................. A61B 5/02
[52] U.S. Cl. ..................................... 272/93; 128/689; 128/700
[58] Field of Search .................. 272/100, DIG. 9, 93; 434/247, 255

[56] References Cited

U.S. PATENT DOCUMENTS

| | | | |
|---|---|---|---|
| 3,492,582 | 1/1970 | Heywood | 434/255 |
| 3,797,010 | 3/1974 | Adler et al. | 272/DIG. 9 |
| 4,232,682 | 11/1980 | Veth | 128/671 |
| 4,281,663 | 8/1981 | Pringle | 128/689 |
| 4,301,808 | 11/1981 | Taus | 128/687 |
| 4,334,544 | 6/1982 | Hill et al. | 128/664 |
| 4,356,825 | 11/1982 | Veth | 128/630 |
| 4,367,752 | 1/1983 | Jimenez et al. | 128/689 |
| 4,409,983 | 10/1983 | Albert | 128/690 |
| 4,517,986 | 5/1985 | Bilgutay | 128/671 |
| 4,566,461 | 1/1986 | Lubell et al. | 128/668 |
| 4,598,700 | 7/1986 | Tamm | 128/671 |
| 4,610,257 | 9/1986 | Furukawa | 128/689 |
| 4,638,807 | 1/1987 | Ryder | 128/644 |

FOREIGN PATENT DOCUMENTS

0117232  9/1979  Japan ........................... 272/DIG. 9

Primary Examiner—Leo P. Picard
Attorney, Agent, or Firm—Chilton, Alix & Van Kirk

[57] ABSTRACT

An exercise aid, worn on the head as a sweatband or built into a helmet or hat, which enhances exercise benefits while minimizing exercise interruptions or distractions. A microcomputer processes heart rate, time and exercise-related inputs and records selected information. A speech synthesizer provides voice output to inform and give instructions to the wearer. Easily located and actuated controls allow convenient operation while actively exercising. Through an interface to an external computer, the device may be programmed to provide the wearer with a customized sequence of instructions and information may be read out for analysis.

27 Claims, 3 Drawing Sheets

PHYSICAL EXERCISE AID

FIELD OF INVENTION

This invention relates to methods of and apparatus suitable for assisting an individual to optimize the benefits of physical exercise. More particularly, the invention provides a portable device for guiding the individual during exercise to optimize exercise benefits while minimizing influences which would be interrupting or distracting. Accordingly, the present invention is directed to novel and improved methods and apparatus of such character.

BACKGROUND OF THE INVENTION

In 1968, Dr. Kenneth Cooper published an article in *Readers Digest* on "aerobics," a method of physical exercise for producing beneficial changes in the respiratory and circulatory systems. One principle of aerobics requires that, to achieve optimum benefit, the subject maintain heart rate within a prescribed range for a prescribed duration. Training and exercising by heart rate has since become a generally accepted practice and, even though it is distracting and inconvenient, participants have learned to stop and take their pulse at intervals during exercise.

Recently, devices have been developed to aid the exerciser. The typical heart monitor is a device which provides a display, usually digital, of a subject's heart rate. A "runner's monitor" is available which senses distance travelled by means of ultrasonic echo, provides a voice output, and provides an input for a heart rate detector.

Heart rate monitors currently available include the following types:
1. Those which are portable.
2. Those which are not portable and are often attached to particular exercise equipment.
3. Those which measure heart rate when requested and require the subject to remain inactive while the reading is taken.
4. Those which measure heart rate continuously while the subject is moving.
5. Those which measure heart rate continuously and provide visual and/or audible alarm signals when the subject's heart rate goes above/below pre-determined limits.
6. Those which include timing functions such as a stop watch.

Since they are display-oriented devices, previously available heart monitors share the drawback of being unable to notify the subject of other than alarm conditions without requiring constant attention to the display. Portable heart monitors have the further disadvantages of a relatively small display which is difficult for an actively exercising person to read (especially one who must wear glasses) and relatively small controls (switches, pushbuttons) which are inconvenient for the active exerciser to locate and actuate. Some also are cumbersome, requiring wires to be connected from one part of the body to another.

The runner's monitor is not appropriate as an aerobic fitness aid since it calculates average heart rate only on command and is, therefore, unable to monitor over-/under heart rate conditions. It does not instruct the user of exercise sequence and is unwieldy in active exercise, requiring a belt-worn electronics package and separate, wire connected, heart rate detector and headphones.

SUMMARY OF THE INVENTION

It is an object of the present invention to provide a portable device which can be worn on the head while exercizing, and that can transmit prerecorded, broadcast, or synthesized audio signals to the user.

It is also an object of the present invention to provide a portable device which will derive and communicate exercise benefit related information (heart rate, time, pace, instructions) to a subject in a manner and form which is compatible with active exercise.

It is another object to minimize interconnection complexity between the input, output, control and processing components of such a device to thereby optimize user comfort and benefit.

It is another object to provide such a device with controls which are easily located and operated by the subject while actively exercising.

It is yet another object to provide such a device with means to present to the subject a sequence of exercise activity related instructions.

It is still another object to provide such a device with means to recognize and to notify the subject of the occurrence and designation of pre-determined conditions.

It is again another object to provide such a device with no moving parts.

It is a further object to provide such a device with a means to record information for subsequent playback.

It is a still further object to provide such a device which can be connected to a computer for the purposes of programming the device's functions, to provide instructions for the subject and to read out information recorded in the device.

These and other objects and advantages are accomplished in accordance with the invention which, when embodied in hardware, is in the form of a band adapted to be secured to the head or built into a hat, helmet, or other headgear of a user. A self-powered data processing unit is carried by the band and programmed to receive input data from the user, perform arithmetic and logic operations on the input data and generate output signals indicative of the user's vital physical signs. A plurality of actuating devices span the band in spaced-apart relationship, each device being capable of generating a respective first type of input data signal to the data processing unit in response to the user's selection of one device by pressing with the finger or hand. A plurality of sensors are associated with the band for generating a second type of input data signal for each of a plurality of user vital signs. A headphone transducer is coupled to the data processing unit, for receiving the generated output signals and producing a voice report at the user's head. By actuating particular activation devices, the user can select a voice report of different vital signs while engaged in physical exercise.

The device can be configured logically into a variety of modes by the user's actuation of one or more pre-determined patterns of the actuating devices. Preferably, at least four configuration modes are available, including a setup mode in which the user can select which vital signs are to be reported and whether the reports are to be imparted at the user's demand, periodically, or when the vital signs fall outside pre-selected limits. A monitoring mode can be selected, in which the reports selected in the setup mode are imparted to the user during physical exercise. An exercise guidance mode provides reports which define, during physical exercise, sequential combinations of desired vital signs or desired periods of time associated with a planned exercise session or routine. A calibration mode is provided in which the user can confirm whether the input data signals from the sensors to the data processing unit are being generated commensurate with the physical manifestations of such vital signs by the user's body.

Preferably, the band, the actuating devices, the sensors, and the transducers are formed in a substantially unitary strip of poly(vinylidene) fluoride plastic, which includes metalized electrical leads.

In another aspect of the invention, the unitary polyfluoride band, or a band of similar piezoelectric material, is configured as a headset, with provision for transducing and controlling audio signals to the user's head, which originate as prerecorded, broadcast, or synthesized input signals.

BRIEF DESCRIPTION OF THE DRAWINGS

The invention will be described below in greater detail with reference to the accompanying drawings, in which.

DESCRIPTION OF THE INVENTION

Figures 1A, 1B, 1C:
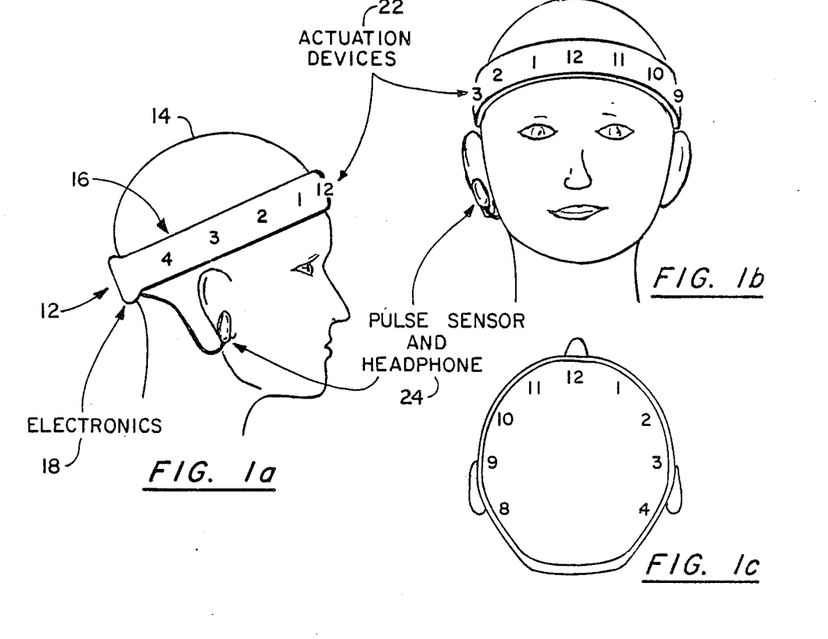
FIGS. 1a, 1b, and 1c show front, side and top views of a subject fitted with the device of this invention.

As shown in FIG. 1, the physical exercise aid 12 of the present invention is worn around the user's head 14 as a headband 16 or sweatband. The band 16 is adjustable o elasticized to fit subjects of different sizes. The band contains electronic components, shown in the block diagram of FIG. 2, housed, for the most part, in an enclosure mounted at the back of the head which together will be referred to hereinafter as electronics 18. The major components not contained in the enclosure are the actuation devices 22 and a pulse sensor-headphone assembly 24.

The actuation devices 22 are momentary switches, e.g., piezoelectric or other devices capable of responding to mechanical pressure to generate an output condition or signal which may be reliably detected by the electronics 18 (similar to keys of a keyboard). To facilitate their operation by an actively exercising subject, the actuation devices are made relatively large compared to normal keyboard keys.

Preferably, the actuation devices are located, and identified, in the manner of the positions on a twelve hour clock. As shown in FIG. 1(c), the 12 o'clock position is in the center of the user's forehead, and, in one implementation of the invention, clock positions 1–4 are spaced apart along the band on the right side of the user's head, and clock positions 8–11 are spaced apart along the left side of the user's head. The electronics 18 is centered at the 6 o'clock position, and may occupy portions of the 5 and 7 o'clock positions.

Figure 2:
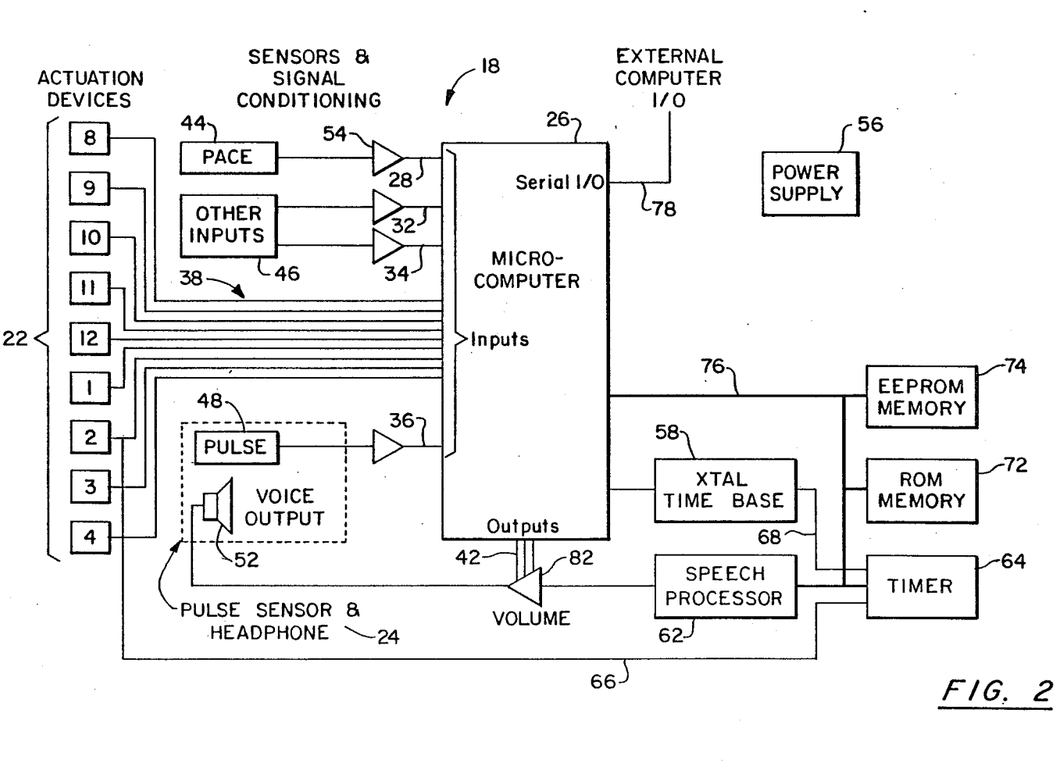
FIG. 2 is a block diagram of the device of this invention.

FIG. 2 shows the block diagram representation of the relationship between the actuation devices 22, the pulse sensor and headphone assembly 24 and the electronics 18. The electronics 18 embodies a self-powered data processing unit which is programmed to receive input data from the user, perform arithmetic and logic operations on the input data, and generate output signals indicative of the user's vital physical signs. Preferably, the data processing unit also receives and stores instructions from the user, and generates output signals in the form of guidance or other information to the user.

In the basic function of the present invention, a plurality of input data pertaining to the user's vital signs, are delivered to a microcomputer 26, on input leads 28, 32, and 36. Lead 28 carries a pace signal, lead 36 carries a heart pulse signal, and leads 32 and 34 may carry other signals, all of which are collectively deemed a type of data signal indicative of the user's "vital signs" i.e., indicative of physical manifestations of the condition or performance of the user's body during exercise.

Each of the actuation devices 22 (of which nine are disclosed in the present embodiment), has a dedicated input lead to the microcomputer 26. The nine leads are collectively identified by reference numeral 38, which represents another type of input data signal, by which the user can set up and control the logical operation of the microcomputer 26.

The primary output signal from the microcomputer is delivered via address and data bus 76 to a speech synthesizer 62, from which a voice signal is generated. The voice signal is appropriately filtered and amplified by operational amplifier 82, the gain of which is controlled by microcomputer outputs 42.

Of course, sensors or the like, such as a pace sensor 44, a pulse sensor 48, and other sensors 46 are connected to their respective signal lines 28, 36 and 32–34. Similarly, a voice output transducer, such as headphone 52, is connected to the line 42. It should be appreciated that, as is conventional in electronic signal processing, suitable operational amplifiers or filters, typified at 54, would be associated with the "vital sign" input data lines.

The electronics 18 also preferably includes several other components, such as a power supply 56 carried on the headband, a crystal controlled clock 58 for generating timing pulses for the microcomputer 26, and for speech synthesizer 62. Preferably, a separate timer 64 is connected, as by line 66, to one of the actuating devices, e.g., #2, and through lead 68, to the crystal time base 58, such that separate timing control associated with the user's exercise routine such as stop watch applications, can be implemented without processing delays in the microcomputer 26.

In the preferred embodiment of the invention, a third type of input, and a second type of output, are also provided. Data storage devices such as ROM memory 72 and EEPROM memory 74 are connected via bus 76 to the microcomputer 26 and speech processor 62, to provide customized logic and instruction capabilities. The customization is accomplished by means of the actuation devices in setup mode and/or by the user's personal computer or other programming device, which is connectable to the microcomputer 26 through the serial input/output port 78. Employing the external computer, the user can override the standard functions and procedures embodied in the firmware of the microcomputer 26, by storing executable instructions in the external memory devices 72, 74.

Likewise, the user may desire that the input or output data associated with a particular period of exercise be recorded in an external device, for long-term record-keeping purposes. Thus, the vital signs type of data, or the control and timing data, may be temporarily stored in a memory device and, at the end of the exercise period, downloaded to the user's computer and exercise database, through the I/O port 78.

The pulse sensor-headphone assembly 24 is also a unique component of this invention. It combines a transducer capable of generating sound, such as a headphone 52, and a sensor 48 capable of detecting, from a body location on or near the headband, each beat of the subject's heart. Such a sensor could use the well-known phenomenon of photoplethysmography, wherein the emission from an infrared source (e.g., an LED) in contact with the skin of the subject is modulated in intensity by the blood flow through the capillaries. The output of a photodiode, positioned to sense the modulated intensity, is a-c coupled, amplified, filtered and clipped to provide pulse signals. Alternatively, piezoelectric or other pressure sensitive devices can be used to sense pressure changes resulting from blood flow in an appendage such as the ear, or at the temple. Output signals could be treated in a manner generally similar to a photoplethysmography sensor.

The pace sensor 44 is an inertial movement detector housed in the electronics 18 to detect vertical movement of the device and, therefore, of the subject's head. Vertical head movement is generally indicative of the pace of the subject when running, walking, bicycling, rowing or exercising in a rhythmic manner. To minimize the effect of movements not related to pace, the detector 44 is damped to respond only to pace rates below 200 per second.

The actuation devices 22 and the pulse and the pace sensors, 48, 44 can employ piezoelectric devices. In addition, piezoelectric materials can be made to generate sound; imposing an audio signal voltage across a piezoelectric material causes it to move or vibrate accordingly. In 1969, H. Kawai reported in the Japanese Journal of Applied Physics, Vol. 8, pages 975–976, that a plastic film, poly(vinylidene) fluoride (PVDF), will exhibit piezoelectric characteristics. The piezoelectric effect in PVDF, utilized in the manufacture of headphones and speakers, was reported in 1976 by M. Tamura, et al. in Journal, Audio Engineering Society, Vol. 23, pages 21–26. The Oct. 23, 1986 issue of Machine Design contained an article: "Piezoelectric Plastics Promise New Sensors," which describes the use of PVDF as pressure sensitive switch elements.

Figure 3A:
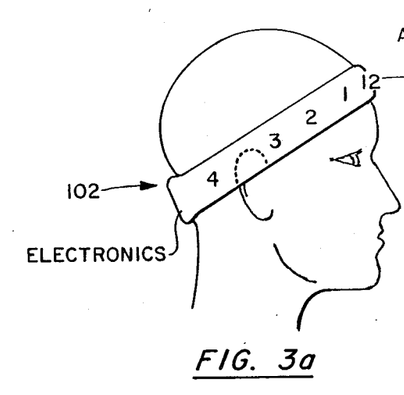
FIGS. 3a, 3b, and 3c show the three views of FIG. 1 for the preferred embodiment of the device of this invention using PVDF film.
Figure 3B:
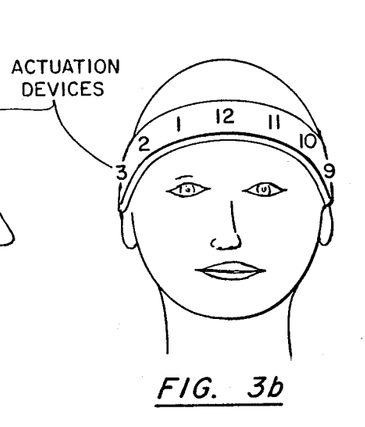
Figure 3C:
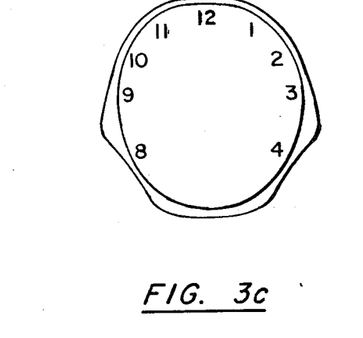
Figure 4:
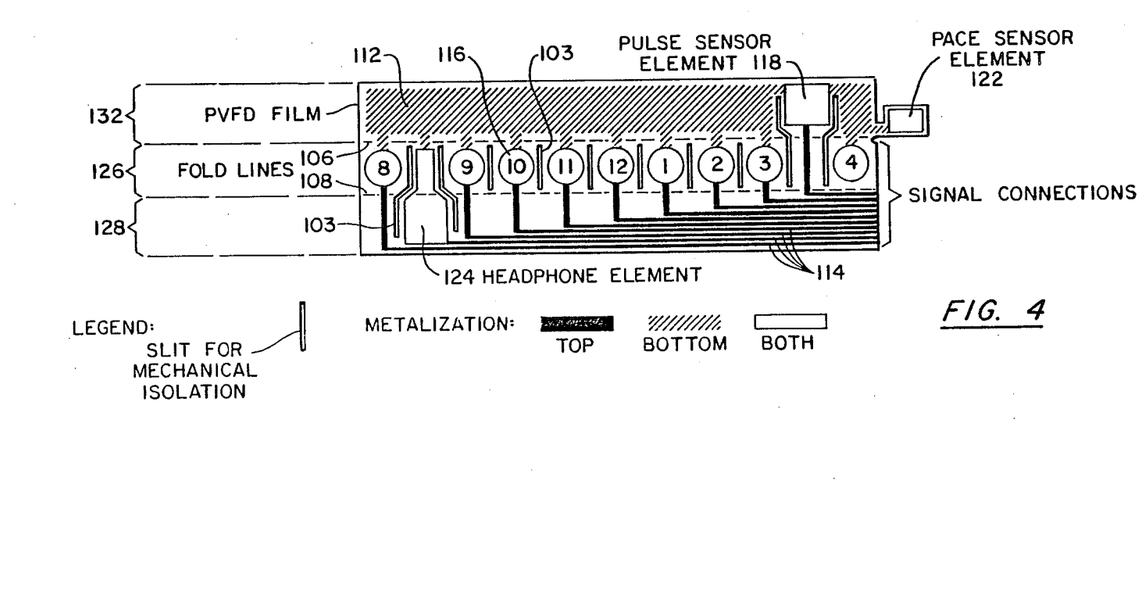
FIG. 4 is a plan drawing of the PVDF film as fabricated for this invention.

FIGS. 3 and 4 illustrate one implementation of the present invention, which takes advantage of such piezoelectric phenomena. The device 102 of this embodiment uses PVDF film with selective metalization and perforations 103 (slits) for mechanical isolation between areas to form multiple, independent signal generation elements, the pulse and pace sensors and the headphone. Combining all of these functions into a single component reduce cost and, since there are minimum moving parts, ruggedness and reliability are enhanced.

Preferably, the PVDF film is an elongated, rectangular strip 104 having a height dimension approximately three times the height of a normal headband or the like. FIG. 4 shows the strip 104 after fabrication, but before folding into the final configuration 102 as worn by the user. The two longitudinal fold lines 106, 108 above and below the actuation devices are shown as broken lines. The film is metalized on both sides, the portion 112 indicated by oblique lines being on the bottom of the film and serving as, in effect, a common ground potential, and the portions 114 on the top side indicated in solid color serving as the electrical signal conducting lines or leads from the actuating devices. Stressing of an actuating device 116, by the finger, produces a piezoelectric potential that is communicated along one of the leads 114 to a corresponding one of the input terminals of the microcomputer (as shown in FIGS. 2). Diodes may be connected to leads 114 to limit the output voltage to levels compatible with the microcomputer.

The pulse sensor element 118 is preferably located to be in contact with the head of the user, to more effectively detect a pulse from the heart beat. Other pulse detection techniques are available, however, such as utilization of piezoelectric material which stretches in response to heartbeat and produces an output signal which can be filtered to remove noise or other background influence.

Figure 5:
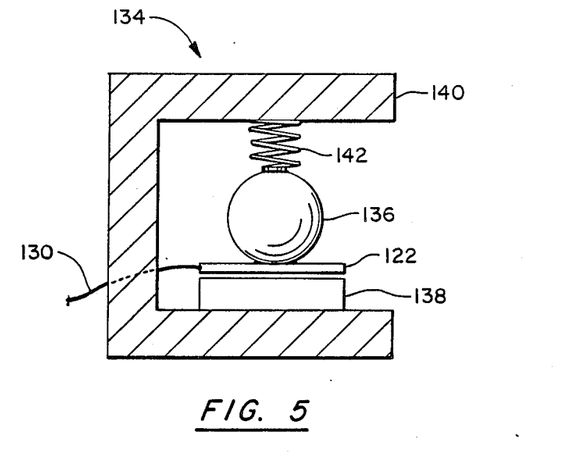
FIG. 5 is a schematic representation of the pace sensor in accordance with the preferred embodiment of the invention.

As shown in FIG. 5, the pace detector 134 preferably consists of a piezoelectric or other pressure sensitive device or substance 122 mounted between a weight 136 and a resilient but fixed base surface 138 in a generally vertical array. The weight is held in contact with the pressure sensitive device by a compressed spring 142 or spongy material. The damping is provided by the combination of the resiliency of the base, the mass of the weight, and the force of the spring. The movement of the subject during exercise generates a force on the mass which urges the piezoelectric 122 material against the resilient layer 138 and thereby generates a potential in the material 122 commensurate with the area stressed by the force of the moving mass. Thus, more vigorous exercise, i.e., greater pace, produces a greater area of stress on the material 122 and thus a higher electric potential which is delivered by lead 130 to the electronics 18 for further processing in accordance with the previous description. The frame 140 of the pace sensor 134 is contained within the enclosure of the electronics 18.

The headphone element 124, unlike the other transducers, spans the central row 126 between the fold lines and crosses one or both fold lines 108, 106 thereby substantially spanning two or three rows. Preferably, the bottom row 128 is folded first, covering the central row 126 of actuating devices 116. Then the top row 132 is folded over the bottom row 128 and central row 126. The resulting band 102, when worn on the head, has the row containing the pulse sensor element 118 on the "inside" of the band against the user's head, the row 126 containing the actuating devices 116 is at the exterior of the band, and the row 128 containing the metalized leads 114 is intermediate the other rows. This folding sequence produces a significant curvature in the headphone element 124, which enables this transducer to enclose a surprisingly large volume of air, and thus generate a louder sound for a given amount of transducer vibration.

Referring again to FIG. 2, the actuation devices 22, sensors 44, 48, and provisions for other input signals 46, such as a bicycle wheel rotation detector, are connected through signal conditioning circuits such as 54 to the inputs 28–38 of microcomputer 26. The actuation device which controls the split time function (shown as actuation device #2) is also connected directly to the input of counter 64.

The microcomputer 26, associated RAM/ROM internal memory and serial input/output components (not shown) may be contained in a single device such as the Texas Instruments TMS7070C02 8-Bit Microprocessor. The speech processor 62 may be the Texas Instruments TSP50C40A which contains an internal ROM capable of storing over 40 seconds of high quality speech; an ample capacity for the vocabulary of approximately sixty words required for the device of this invention. The external ROM 72 shown in FIG. 2 is optional to facilitate programming of the device for custom applications. The EEPROM 74 or, alternately, a low power (CMOS) RAM permanently powered by a long life battery, is used as non-volatile memory to store both the subject's performance data while exercising and program code input to the device either through setup mode or through the serial interface from an external computer.

The actuation devices 22 are arranged around the device headband 16 at positions which are readily located and tapped. These actuation devices initiate all user operations; each actuation is confirmed by appropriate voice response. The following is one example of implementation:

As shown in FIG. 1, nine actuation devices 22 are numbered according to clock face positions with the 12 o'clock position located in the center of the forehead. Actuation devices #8 and #4 are reserved to respectively decrease/increase sound level one volume unit whenever touched. The device can be configured to operate in multiple modes. To minimize inadvertent mode selection while exercising, modes are selected by touching two separated actuation devices simultaneously.

1. Setup Mode.

The device in setup mode allows the user to enter initial parameters and operating conditions.

To enter setup mode, actuation devices #8 and #4 are touched simultaneously. This initiates a sequence of parameters which may be set or changed by the user. The parameter and its current value or setting is announced and the user may change the value or setting if desired. Actuation devices #9 and #10 decrement the current value, #9 by a larger amount than #10; actuation devices #3 and #2 increment the value in the same manner. By touching actuation device #12, the new value or setting is entered and the setup procedure is sequenced to the next parameter. Setup mode may be terminated at any point by again touching actuation devices #8 and #4.

| AD # | VOICE RESPONSE | CHANGE BY AD # 9/3 | 10/2 | VOICE RESPONSE(S) |
|---|---|---|---|---|
| 8 & 4 | SETUP, PULSE, HIGH, (VALUE) | −/+10 | −/+1 | (NEW VALUE) |
| 12 | SETUP, PULSE, LOW, (VALUE) | −/+10 | −/+1 | (NEW VALUE) |
| 12 | SETUP, PULSE, REPORT, (STATUS) | SEQUENCE: DEMAND-PERIODIC-LIMITS- | | (NEW STATUS) |
| 12 | SETUP, TIME, WARMUP, (TIME) | −/+MIN | −/+ SEC | (NEW TIME) |
| 12 | SETUP, TIME, EXERCISE, (TIME) | −/+MIN | −/+ SEC | (NEW TIME) |
| 12 | SETUP, TIME, COOLOFF, (TIME) | −/+MIN | −/+ SEC | (NEW TIME) |
| 12 | SETUP, TIME, REPORT, (STATUS) | SEQ:DEMAND-PERIODIC- | | (NEW STATUS) |
| 12 | SETUP, BEAT, ONE, (VALUE) | −/+10 | −/+1 | (NEW VALUE) |
| 12 | SETUP, BEAT, TWO, (VALUE) | −/+10 | −/+1 | (NEW VALUE) |
| 12 | SETUP, BEAT, THREE, (VALUE) | −/+10 | −/+1 | (NEW VALUE) |
| 12 | SETUP, PACE, REPORT, (STATUS) | SEQ:DEMAND-PERIODIC- | | (NEW STATUS) |
| 12 | SETUP, PERIODIC, REPORT, (TIME) | −/+MIN | −/+SEC | (NEW TIME) |
| 8 & 4 | SETUP, COMPLETE | | | |

2. Pulse Monitor Mode

The device in pulse monitor mode:

notifies the subject of his/her pulse rate as selected either periodically or on demand or only when the pulse rate goes above or below present limits, and notifies the subject of the elapsed time as selected either periodically or on demand, and notifies the subject of "split" times on demand (elapsed time between subject controlled start/stop signals), and generates a metronome beat at selected rate(s) for pace or cadence on demand, and notifies the subject of other information (e.g., distance, speed, subject pace rate, etc.) as selected either periodically or on demand, and stores information such as maximum, minimum heart rates, split times, conditions at subject-entered milestones, etc. for recall on demand.

As an example, pulse monitor mode could be implemented by touching actuation devices #9 and #3 simultaneously. The device resets the elapsed and split time counters and begins operation according to setup conditions. At any time, the user can demand reports by touching the actuation device positions assigned to the desired information. If LIMITS had been chosen for pulse in setup mode, heart rate will be reported at the periodic time interval selected until the heart rate exceeds the lower limit. The heart rate will not be announced again until it exceeds or falls below the limits set.

| AD # | FUNCTION | VOICE RESPONSE | DESCRIPTION |
|---|---|---|---|
| 9 & 3 | PULSE MONITOR MODE | PULSE MONITOR | RESETS TIMES, STARTS PERIODIC REPORTS AS SET UP |
| 8 | DECREASE VOLUME | | VOLUME DECREASES |
| 9 | SPEED/DISTANCE | SPEED (VALUE) DISTANCE (VALUE) | GIVES VALUE - SEQUENTIALLY |
| 10 | MILESTONE | MARK | SAVES PULSE, TIME, PACE |
| 11 | HEART RATE | HEART (VALUE) | GIVES CURRENT RATE |
| 1 | TIME | TIME (ELAPSED TIME) | GIVES TIME SINCE START |
| 2 | SPLIT TIME | SPLIT (SPLIT TIME) | GIVES TIME SINCE LAST SPLIT STARTS TIMING NEW SPLIT |

| AD # | FUNCTION | VOICE RESPONSE | DESCRIPTION |
|---|---|---|---|
| 3 | PACE | PACE (VALUE) | GIVES CURRENT PACE RATE |
| 4 | INCREASE VOLUME | | VOLUME INCREASES |
| 8 & 9 | METRONOME BEAT 1 | BEAT (VALUE 1) | SOUNDS AT BEAT ONE RATE |
| 9 & 10 | METRONOME BEAT 2 | BEAT (VALUE 2) | SOUNDS AT BEAT TWO RATE |
| 10 & 11 | METRONOME BEAT 3 | BEAT (VALUE 3) | SOUNDS AT BEAT THREE RATE |
| ANY | METRONOME STOP | | TERMINATES BEAT |
| 1, 12 and 11 | IGNORE | N/A | DISABLES AD SPOTS (PERIODIC REPORTS CONTINUE) ENABLED AGAIN BY ADs #9 and #3 |
| 2 & 3 | RECALL | SPLIT (SPLIT TIMES) MARK(MILESTONES' DATA) | STORED DATA RECALLED SEQUENTIALLY BY AD #12. TERMINATED BY ADs #2 and #3. |

3. Standard Exercise Mode

The device in standard exercise mode guides the subject through warm-up, full exercise and cool-off periods. It:

allows the duration for each period to be pre-selected in setup mode, and starts each period on request of the subject, and allows each period to be reset and restarted on request of the subject, and allows each period to be halted and the next period begun on request of the subject, and allows selection of elapsed or "quality" time for the full exercise period where "quality" time is the duration the subject's heart rate was above the lower limit, and provides all the functions of the pulse monitor mode, and stores information on resting heart rate and recovery time vs. heart rate for recall on demand.

As an example, standard exercise mode could be initiated by touching actuation devices #10 and #12 simultaneously. All the functions of pulse monitor mode are available, plus, the device "talks" the subject through warmup, exercise and cooldown periods. At the conclusion of each period, the subject begins the next period by again touching actuation devices #10 and #12. The subject may reset to the beginning of any period by touching actuation device #12.

4. Programmed Exercise Mode

The device in programmed exercise mode guides the subject through periods of changing exercise requirements. It:

allows the conditions for each period to be programmed prior to use through connection to a computer, and allows programming to be accomplished at a functional level using the functions available in the pulse monitor and standard exercise modes, and provides the operating functions of the pulse monitor and standard exercise modes, and allows programming to be accomplished at assembly language level to add other functions.

Programmed exercise mode could replace the standard exercise mode and therefore be initiated and advanced through the programmed sequence by the same actuation devices #10 and #2.

5. Test/Calibrate Mode

Test/calibrate mode can be entered/exited at any time except during setup mode. This mode allows the subject to check the operation of the device before or while exercising and it provides a means to calibrate pace signals for subsequent speed and distance calculation and report. It:

provides audible beats corresponding to detected heart beats to confirm proper operation and positioning of the heart rate sensor, and provides audible beats corresponding to detected pace to confirm proper operation and positioning of the pace sensor, and provides audible beats corresponding to detected external input, and provides a means to calibrate pace or external input (e.g., bicycle wheel rotation) with a known distance travelled.

For example, the test/calibration mode could be entered by touching both actuation devices #11 and #1 simultaneously. For convenience, functions within the test/calibration mode could be invoked by touching the same actuation device assigned in the pulse monitor and exercise modes.

| AD # | FUNCTION | VOICE RESPONSE | DESCRIPTION |
|---|---|---|---|
| 11 & 1 | TEST MODE | TEST | ENTER TEST/CALIB. MODE |
| 9 | START DISTANCE CALIB. | MILES, START, TONE | BEGINS CALIBRATION SOUNDS TONE AS REMINDER |
| 10 | END DISTANCE CALIB. AD #3 INCREMENTS: AD #9 DECREMENTS: AD #12 ENTERS. | ENTER MILES ONE-TWO-THREE--THREE-TWO-CAL | REQUIRES ENTRY OF DISTANCE IN MILES CALIB COMPLETE; TONE OFF |
| 11 | TEST HEART RATE SENSOR | HEART (BEATS) | SOUNDS BEATS AS SENSED |
| 1 | TEST EXTERNAL INPUT | INPUT (BEATS) | SOUNDS BEATS AS INPUT |
| 3 | TEST PACE | PACE (BEATS) | SOUNDS BEATS AS DETECTED |
| 11 & 1 | EXIT TEST MODE | TEST OFF | RESTORES PREVIOUS MODE; CALIB CONTINUES IF ON WITH TONE AS REMINDER. |

The preferred form of the invention is, as described above, an exercise aid that is customized by the user's selection of a setup or other configuration mode. In a broader aspect, the invention is directed to a headset for communicating information to a subject, whereby the user can actuate binary switches on a headband, to control the content or other characteristics of an audible report or signal commensurate with an analogue phenomena of interest to the user. For example, the analogue phenomena could be electromagnetic waves carrying a broadcast radio program, instructions carried on a magnetic tape playing in a cassette player/recorder, or, as in the preferred embodiment described above, data indicative of the user's vital signs or instructions originating from a computer or data storage device. Thus, a microprocessor or the like is provided for receiving binary data of a first type generated by the user's selection of one or more actuation devices. Input data of the second type, which is commensurate with a sensed analogue phenomena of interest to the subject, is also processed by a second portion of the same, or by a different processor. The second processor need not be a digital device, but could be a simple radio processing electromagnetic signal. The microprocessor then performs the required logic operations on the input data of the second type or on the audible signal to the user, in accordance with the control dictated by the user through the actuation of the actuation devices.

I claim:

1. An interactive headset for selectively communicating audible information to a user comprising:
   a band adapted to be worn on the head of the user;
   self-powered digital first processing means carried by said band and programmed to receive input signals, perform arithmetic and logical operations in response to the input signals, and generate a digital output signal;
   a plurality of actuation devices integral with and spanning said band in spaced-apart relationship, each actuation device being capable of generating an input signal to said first processing means in response to actuation by the user; and
   second processing means operatively connected to said first processing means and responsive to output signals generated by said first processing means, for generating an audible voice report to the user;
   whereby the user can control the audible voice report by selectively actuating the actuation devices.

2. The headset of claim 1 wherein said first processing means includes means for detecting at least one real time parameter commensurate with one of the user's vital signs and generating a signal commensurate therewith and means for digitizing the signals commensurate with the detected vital signs.

3. The headset of claim 2 wherein the first processing means includes a microcomputer and the second processing means shares at least a portion of said microcomputer.

4. The headset of claim 3 wherein the second processing means is also carried by the headband.

5. The headset of claim 3 wherein said first processing means includes means for storing information and reading the stored information, and wherein said second processing means includes means for converting the information read by said first processing means into audible voice signals commensurate therewith.

6. The headset of claim 5 wherein said first processing means generates at least two types of digital control signals in response to inputs from said actuation devices, including a first type of signal for selecting which recorded information will be converted to audible voice signals and a second type of signal for selecting which detected real time parameter signals will be converted to audible voice.

7. The headset of claim 6 wherein the first processing means generates a third type of digital control signal in response to the binary input from the actuation devices, for raising or lowering the volume of the audible voice signal.

8. The headset of claim 1 wherein said first processing means includes means for storing information and reading the stored information, and wherein said second processing means includes means for converting the information read by said first processing means into audible voice signals commensurate therewith.

9. The headset of claim 1 wherein the second processing means includes a headphone element integral with the band and contoured to enclose a volume of air.

10. The headset of claim 9 wherein the headphone is in the form of a piezoelectric transducer.

11. The headset of claim 1 wherein each of said actuation devices is in the form of a piezoelectric transducer which produces an input signal for said first processing means in response to momentary user contact therewith.

12. An exercise aid comprising:
   a band adapted to be worn on the head of a user;
   self-powered data processing means carried by said band and programmed to receive input data from the user, perform arithmetic and logic operations in response to the received input data and generate output signals indicative of physical exercise related information;
   a plurality of actuation devices integral with and spanning said band in spaced-apart relationship, each actuation device being capable of generating a respective first type of in put data signal for said data processing means in response to actuation by the user;
   a plurality of input terminals on said band for connection to user state related parameter sensor means whereby a second type of input data signal may be provided to said data processing means; and
   means electronically coupled to said data processing means for receiving the output signals generated thereby and producing a corresponding voice report audible to the user;
   whereby the user can select a voice report of physical exercise related information while engaged in physical exercise.

13. The exercise aid of claim 12 wherein said data processing means further includes means for storing physical exercise related information including instructions relating to the conditions under which voice reports will be produced.

14. The exercise aid of claim 13, wherein said data processing means is programmed to recognize a plurality of distinct sequences of the first type of input data signal, and in response to configure a corresponding plurality of sequences of voice reports.

15. The exercise aid of claim 14 wherein the sensor means connected to said plurality of input signals provide input data signals commensurate with vital signs of the user and wherein each of said configurations corresponds to a different operating mode of the exercise aid, said modes including:
   a set-up mode in which the user can select which vital signs are to be reported and whether the reports are to be produced at the user's demands, periodically or when the vital signs fall outside preselected limits, and a monitoring mode in which the reports selected in the set-up are produced during physical exercise.

16. The exercise aid of claim 15, wherein said modes further include an exercise guidance mode in which reports are produced during exercise to inform the user of the desired vital signs for desired periods of time associated with a planned exercise session.

17. The exercise aid of claim 15, wherein said modes further include a calibration mode in which the user can confirm whether the second type of input data signals are generated commensurate with the respective vital signs of the user.

18. The exercise aid of claim 13 wherein said data processing means includes a data port whereby communication with an external computer may be established.

19. The exercise aid of claim 12 wherein said means for receiving output signals and producing a voice report are carried in said band.

20. The exercise aid of claim 12 wherein said sensors include a sensor for each of the vital signs of heart pulse and body pace.

21. The exercise aid of claim 20 wherein the pulse sensor, the pace sensor, and the actuation devices each includes a piezoelectric transducer.

22. The exercise aid of claim 20 wherein said body pace sensor includes a frame for displacement commensurate with the pace of physical activity;

a base member mounted on said frame and having a resilient surface;

spring means suspended from said frame above said base member resilient surface, said spring means having a mass coupled to said frame with a spring constant such that the mass has a rest position above said resilient surface and during physical activity is displaced downwardly toward said resilient surface;

a piezoelectric layer interposed between said spring means mass and said resilient layer whereby said piezoelectric layer is deformed as the mass reaches its maximum displacement towards said resilient layer, the deformation of said piezoelectric layer being commensurate with the momentum of the mass as it is displaced by the physical activity; and means for sensing the change in the electrical potential generated by said piezoelectric layer as it is deformed by the mass, the rate of such changes in potential being indicative of the pace of physical activity.

23. The exercise aid of claim 12 wherein said means for producing a voice report includes a piezoelectric transducer.

24. The exercise aid of claim 12 wherein said band is constructed of piezoelectric material and said band includes means for physically delineating the actuating devices, sensors, and means for imparting a voice report from each other, and metallized means for electrically connecting each of them to said data processing means.

25. The exercise aid of claim 24, wherein said band includes a substantially unitary strip folded longitudinally to form substantially parallel, side-by-side, rows.

26. The exercise aid of claim 25 wherein the piezoelectric voice report transducer is integrally formed in said band oriented generally transversely to the fold lines and spans more than one of said rows, thereby enclosing a volume of air.

27. The exercise aid of claim 24 wherein each of said actuation devices is delineated from the other by stress isolating means.

* * * * *